US012697012B2

(12) United States Patent (10) Patent No.: US 12,697,012 B2
Luis et al. (45) Date of Patent: Aug. 4, 2026

(54) REUSE PREVENTION FOR SINGLE-USE VALVES FOR MEDICAL DEVICES

(71) Applicant: Boston Scientific Scimed, Inc., Maple Grove, MN (US)

(72) Inventors: Brian Luis, Worcester, MA (US); Pauline R. Limberg, Northborough, MA (US); Ryan Vincent William Pollock, Leominster, MA (US); Nathan T. Cummings, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 669 days.

(21) Appl. No.: 17/480,857

(22) Filed: Sep. 21, 2021

(65) Prior Publication Data

US 2022/0095894 A1 Mar. 31, 2022

Related U.S. Application Data

(60) Provisional application No. 63/084,869, filed on Sep. 29, 2020, provisional application No. 63/084,863, filed on Sep. 29, 2020.

(51) Int. Cl.
*A61B 1/00* (2006.01)
*A61B 1/015* (2006.01)
(Continued)

(52) U.S. Cl.
CPC .......... *A61B 1/00068* (2013.01); *A61B 1/015* (2013.01); *A61M 39/22* (2013.01); *F16K 37/0008* (2013.01); *A61M 2205/584* (2013.01)

(58) Field of Classification Search
CPC .... A61B 1/00068; A61B 1/015; A61M 39/22; A61M 2205/584
See application file for complete search history.

(56) References Cited

U.S. PATENT DOCUMENTS 3,828,746 A * 8/1974 De Martelaere ....... F02M 26/66
123/568.29
6,874,517 B2 4/2005 Halstead et al.
(Continued)

FOREIGN PATENT DOCUMENTS

EP 3073889 B1 4/2019
JP 2006-175175 A 7/2006
(Continued)

OTHER PUBLICATIONS

Porex Filtration Group®, "POREX® Medical Materials and Filters" Porex Corporation, 6 pages, 2018.
(Continued)

*Primary Examiner* — Michael J Carey
*Assistant Examiner* — Megan Elizabeth Monahan
(74) *Attorney, Agent, or Firm* — Seager, Tufte & Wickhem, LLP

(57) ABSTRACT

The cleaning valves (or valves) of the current disclosure are generally single-use devices (SUDs) and therefore disposable. Reusing SUDs can be disadvantageous, as single-use devices are not designed to be reusable. Accordingly, valves (or valve assemblies) for medical devices, such as endoscopes, disclosed may be configured to transition from a first state to a second state in response to utilization of the valve, e.g., to control fluid flow through a valve well. The transition from the first state to the second state may prevent reuse of valves of the present disclosure. For instance, a lumen between first and second orifices in a valve stem may be blocked or disconnected.

19 Claims, 6 Drawing Sheets

(51) Int. Cl.
  A61M 39/22 (2006.01)
  F16K 37/00 (2006.01)

(56) References Cited

U.S. PATENT DOCUMENTS

| | | | | |
|---|---|---|---|---|
| 10,174,855 B2 * | 1/2019 | Michnevitz | ............ | F16K 17/383 |
| 2004/0238014 A1 | 12/2004 | Halstead et al. | | |
| 2006/0184154 A1 * | 8/2006 | Moberg | ............ | A61M 5/16854 |
| | | | | 604/151 |
| 2012/0071843 A1 * | 3/2012 | Yamane | ............... | A61M 1/7411 |
| | | | | 604/319 |
| 2015/0144215 A1 * | 5/2015 | Bellofatto | ........... | F16K 11/0712 |
| | | | | 137/625.69 |
| 2020/0016637 A1 | 1/2020 | Still et al. | | |
| 2020/0187756 A1 | 6/2020 | Maurice | | |

FOREIGN PATENT DOCUMENTS

| | | | |
|---|---|---|---|
| JP | 2016-539695 | A | 12/2016 |
| JP | 2018-164565 | A | 10/2018 |
| WO | 2010-101149 | A1 | 9/2010 |
| WO | 2015080694 | A1 | 6/2015 |
| WO | 2016185208 | A1 | 11/2016 |
| WO | 2020243421 | A1 | 12/2020 |

OTHER PUBLICATIONS

International Search Report and Written Opinion for the International Patent Application No. PCT/US2021/051306 mailed Jan. 19, 2022, 14 pages.

U.S. Appl. No. 16/868,325, titled Devices, Systems, Methods and Designs for Medical Cleaning Valves, filed May 6, 2020.

U.S. Appl. No. 16/868,329, titled Devices, Systems, Methods and Designs for Medical Cleaning Valves, filed May 6, 2020.

* cited by examiner

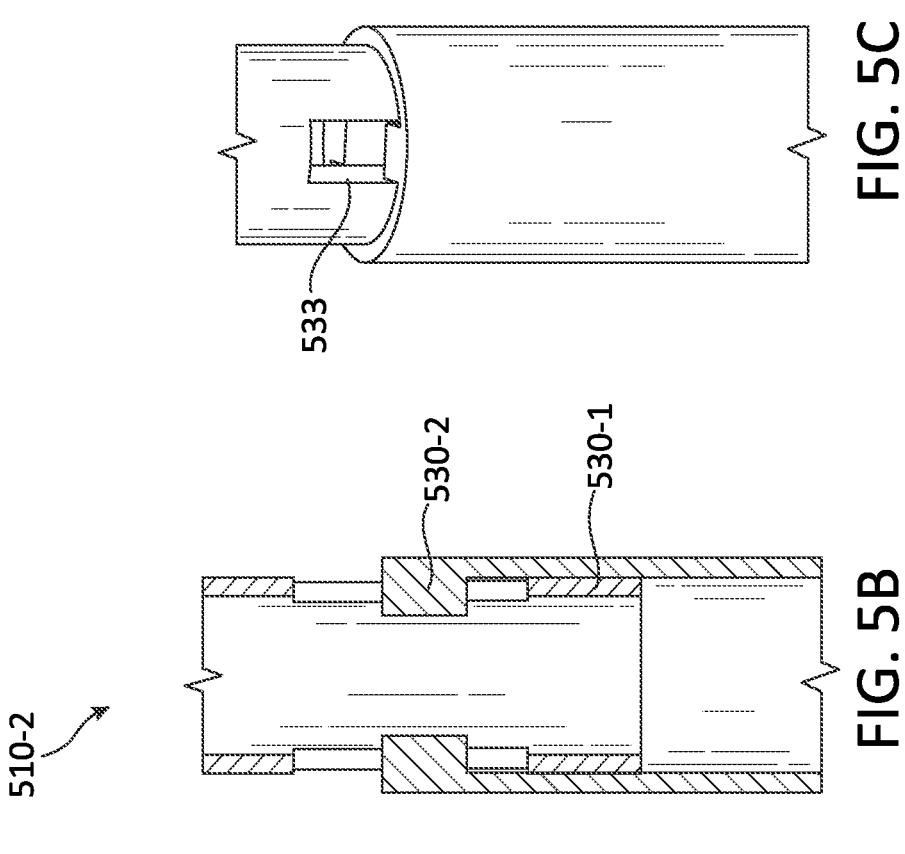
FIG. 5C
FIG. 5B
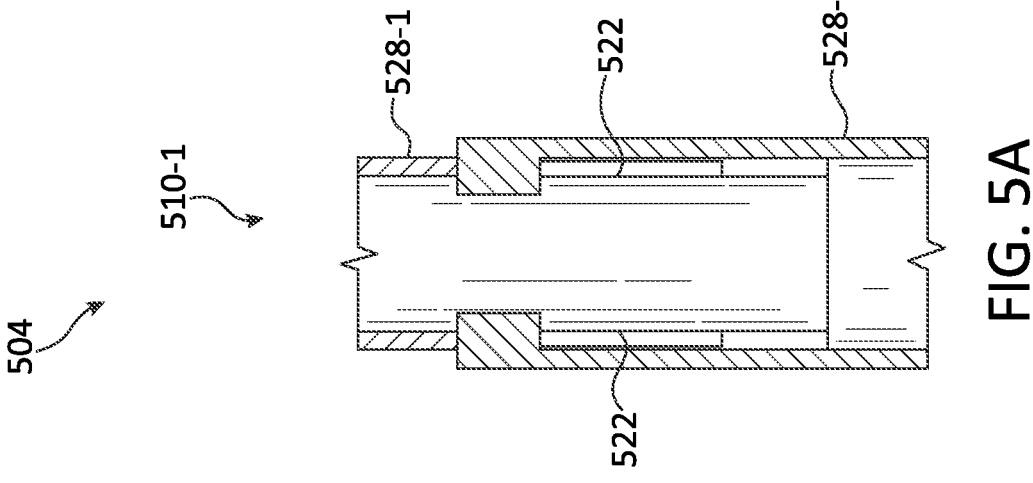
FIG. 5A

REUSE PREVENTION FOR SINGLE-USE VALVES FOR MEDICAL DEVICES

PRIORITY

The present application claims the benefit of priority under 35 U.S.C. § 119 to U.S. Provisional Application Ser. Nos. 63/084,869 and 63/084,863, each filed Sep. 29, 2020, the disclosures of which are incorporated herein by reference in their entirety.

FIELD

The present disclosure relates generally to valves for medical devices. In particular, the present disclosure relates to cleaning valves for medical devices.

BACKGROUND

Endoscopes include functionality to deliver fluids and suction at a site of a procedure. Tubing for delivering fluids and/or suction extends from a handle of the endoscope, through a shaft of the endoscope, and to a distal tip of the endoscope. During a procedure, body fluids, tissues, or other material can build up in the tubing. In order to aid in reprocessing of reusable endoscopes between procedures, pre-processing is performed in an endoscopy suite. For example, water or other fluids are flushed through the tubing after the endoscope is removed from a patient, in order to clear debris from the air/water and/or suction tubing. The cleaning valve may be inserted into an air/water valve cylinder (i.e., valve well) of an endoscope after the scope is removed from a patient and the procedure valve is removed from the valve cylinder. An operator may then depress a button of the cleaning valve for a predetermined amount of time to flush the air and/or water channels of the endoscope prior to further reprocessing of the endoscope. An important aspect of a single-use valve that it is not inadvertently reused. Another important aspect of a cleaning valve is that it is not confused with a procedural valve and inadvertently used in place thereof during a procedure when the scope is inserted within a patient. It is with all of the above considerations in mind that the improvements of the present disclosure may be useful.

SUMMARY

In one aspect, the present disclosure relates to a valve assembly for controlling fluid flow through valve wells. The valve assembly may include comprising an interface member and a valve stem to which the interface member is removably couplable. The valve stem may include a proximal portion, a distal portion, two or more orifices, and a lumen in fluid communication with first and second orifices of the two or more orifices. The valve assembly may be configured to transition from a first state to a second state in response to utilization of the valve assembly to control fluid flow through a valve well. The second state of the valve assembly may prevent utilization of the valve assembly to control fluid flow through valve wells.

In some embodiments, fluid communication between the first and second orifices via the lumen is blocked in the second state. In various embodiments, the lumen includes a transition deposit comprising a material configured to expand and fill a portion of the lumen when the material is exposed to a liquid. In many embodiments, the proximal and distal portions of the valve stem decouple to transition from the first state to the second state. In several embodiments, the proximal and distal portions of the valve stem are connected by a retention linkage and a separation linkage in the first state and the proximal and distal portions of the valve stem are connected by the retention linkage and not the separation linkage in the second state. In several such embodiments, the separation linkage or the retention linkage is disposed within the lumen. In some such embodiments, the separation linkage or the retention linkage is disposed outside of the lumen. In various such embodiments, the separation linkage comprises a loop disposed on a distal end of the proximal portion of the valve stem or on a proximal end of the distal portion of the valve stem. In multiple embodiments, utilization of the valve assembly to control fluid flow through a valve well comprises one or more of insertion of the valve stem into the valve well, controlling fluid flow through the valve well, and removal of the valve stem from the valve well. In some embodiments, the proximal portion of the valve stem is fixed relative to the distal portion of the valve stem by a molded weak point in the first state, and the proximal portion of the valve stem is slidably coupled to the distal portion of the valve stem in the second state. In some such embodiments, utilization of the valve assembly to control fluid flow through the valve well breaks the molded weak point to transition the valve assembly from the first state to the second state. In various embodiments, the proximal portion of the valve stem is fixed relative to the distal portion of the valve stem by a transition deposit in the first state, and the proximal portion of the valve stem is slidably coupled to the distal portion of the valve stem in the second state. In various such embodiments, exposure of the transition deposit to a liquid from utilization of the valve assembly to control fluid flow through the valve well dissolves the transition deposit to transition the valve assembly from the first state to the second state. Many embodiments include a plurality of radial legs with first and second ends and the first ends are pivotally connected to the valve stem. In many such embodiments, the second ends are retained proximate to the valve stem by a hat slidably coupled to the valve stem in the first state and the second ends are released by the hat in the second state.

In another aspect, the present disclosure relates to a system comprising a valve well and a valve assembly. The valve well may include a cavity with two or more ports. The valve assembly may be for controlling fluid flow through valve wells. The valve assembly may include a valve stem and an interface member. The valve stem may include a proximal portion, a distal portion, two or more orifices, and a lumen in fluid communication with first and second orifices of the two or more orifices. The interface member may be coupled to the valve well and the valve stem. The valve assembly may be configured to transition from a first state to a second state in response to utilization of the valve assembly to control fluid flow through the valve well. The second state of the valve assembly may prevent utilization of the valve assembly to control fluid flow through valve wells.

In some embodiments, utilization of the valve assembly to control fluid flow through the valve well comprises one or more of insertion of the valve stem into the valve well, controlling fluid flow through the valve well, and removal of the valve stem from the valve well. In various embodiments, fluid communication between the first and second orifices via the lumen is blocked in the second state. In many embodiments, the proximal and distal portions of the valve stem decouple to transition from the first state to the second state.

In yet another aspect, the present disclosure relates to a method. The method may include one or more of: exposing a valve assembly to a valve well; and transitioning the valve assembly from a first state to a second state by exposing the valve assembly to the valve well, wherein the second state of the valve assembly prevents utilization of the valve assembly to control fluid flow through valve wells. In some embodiments, exposing the valve stem to the valve well comprises one or more of inserting the valve stem into the valve well, controlling flow of a fluid through the valve well with the valve stem, and removing the valve stem from the valve well:

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 5A-5C illustrate various aspects of exemplary valve stem portions according to one or more embodiments disclosed hereby.

DETAILED DESCRIPTION

Figure 1:
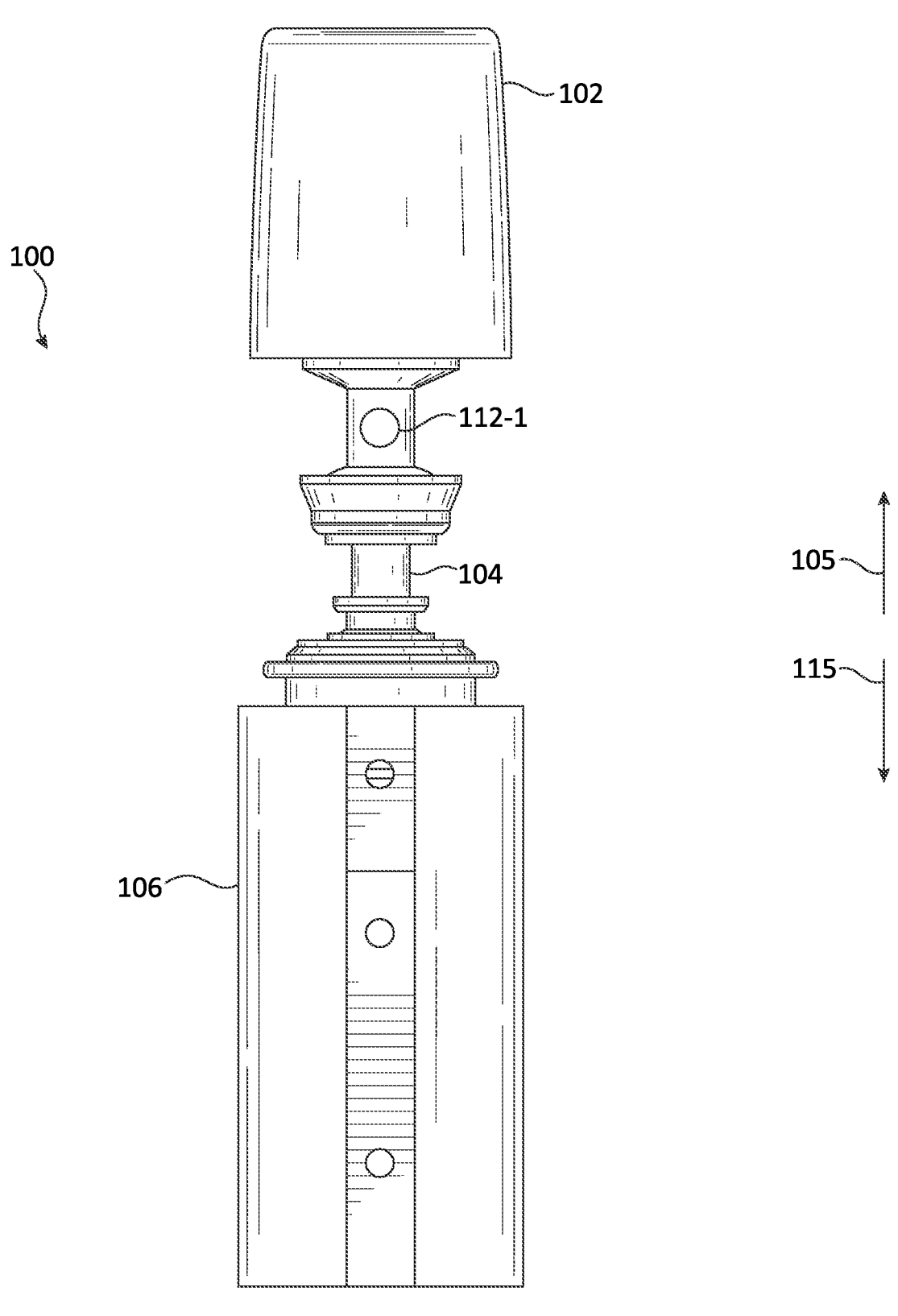
FIG. 1 illustrates an exemplary valve assembly in conjunction with a valve well according to one or more embodiments disclosed hereby.

A medical cleaning valve (or cleaning valve) may be configured to provide cleaning functionality to air and water channels of an endoscope. In a first configuration, the cleaning valve may provide a continuous feed of air to both air and water channels in a handle and shaft of an endoscope, and through an air/water nozzle at the distal end of the endoscope. In a second configuration, the cleaning valve may feed water into the air channel in the handle and shaft of the endoscope, and through the air nozzle at the distal end of the endoscope. The cleaning valves (or valves) of the current disclosure are generally single-use devices (SUDs) and therefore disposable. Reusing SUDs that are not designed for reprocessing and reuse can result in unnecessary exposure to bacteria. Accordingly, many valves (or valve assemblies) disclosed hereby may be configured to transition from a first state to a second state in response to utilization of the valve to control fluid flow through a valve well. The transition from the first state to the second state may prevent reuse in of one or more valves disclosed hereby. For instance, a lumen between first and second orifices in a valve stem may be blocked or disconnected.

Further, the valve may be made from a limited number of parts and materials, e.g., to limit its cost, so that it may be economically disposable. For example, an interface member may seal an opening to the lumen of the valve. In yet another example, the valve may have a single elastomeric component, or spring cap. Additionally, cleaning valves may have a similar appearance to procedural valves. However, using a cleaning valve in place of a procedural valve may result in fluid flow through an incorrect endoscope channel, e.g., liquid being delivered through the air channel. Also, using a cleaning valve in place of a procedural valve may result in continuous insufflation of air into a patient, such as via both the air and water channels. Accordingly, one or more embodiments disclosed hereby may include cleaning valves with features and/or components that facilitate differentiating them from procedural valves.

It may be understood that the disclosure included herein is exemplary and explanatory only and is not restrictive. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the term "proximal" means a direction closer to a surface used by an operator for operating a valve (e.g., an interface member, a user interface, a button) and the term "distal" means a direction away from the surface used by an operator for operating a valve (e.g., a button). Regarding FIGS. 1-6B, "proximal" may refer to towards the top of the drawing sheet and "distal" may refer to towards the bottom of the drawing sheet. Although endoscopes are referenced herein, reference to endoscopes or endoscopy should not be construed as limiting the possible applications of the disclosed aspects. For example, the disclosed aspects may be used with duodenoscopes, bronchoscopes, ureteroscopes, colonoscopes, catheters, diagnostic or therapeutic tools or devices, or other types of medical devices. Additionally, although cleaning valves are referenced herein, reference to cleaning valves should not be construed as limiting the possible applications of the disclosed aspects. For example, the disclosed aspects may be used with a variety of medical valves for controlling the flow of fluids.

Reference is now made to the drawings, wherein like reference numerals are used to refer to like elements throughout. In the following description, for purpose of explanation, numerous specific details are set forth in order to provide a thorough understanding thereof. It may be evident, however, that the novel embodiments can be practiced without these specific details. In other instances, well known structures and devices are shown in block diagram form to facilitate a description thereof. The intention is to cover all modification, equivalents, and alternatives within the scope of the claims.

FIG. 1 illustrates various aspects of a valve assembly 100 in conjunction with a valve well 106 according to one or more embodiments of the present disclosure. The valve assembly 100 may include an interface member 102 and a valve stem 104 with orifice 112-1. More generally, a valve assembly may refer to an interface member in conjunction with a valve stem. In various embodiments, the valve assembly 100 may be inserted into and/or coupled with the valve well 106. The valve assembly 100 and valve well 106 may be oriented with proximal end 105 and distal end 115. In many embodiments, the interface member 102 may be interacted with to move the valve stem 104 proximally or distally within the valve well 106 to control the flow of fluid through the valve well 106. For instance, valve assembly 100 may be utilized to route water to flush out one or more tubes and/or lumens in an endoscopic system. In some embodiments, FIG. 1 may include one or more components that are the same or similar to one or more other components of the present disclosure. Further, one or more components of FIG. 1, or aspects thereof, may be incorporated into other embodiments of the present disclosure without departing from the scope of this disclosure. Embodiments are not limited in this context.

Figures 2A, 2B:
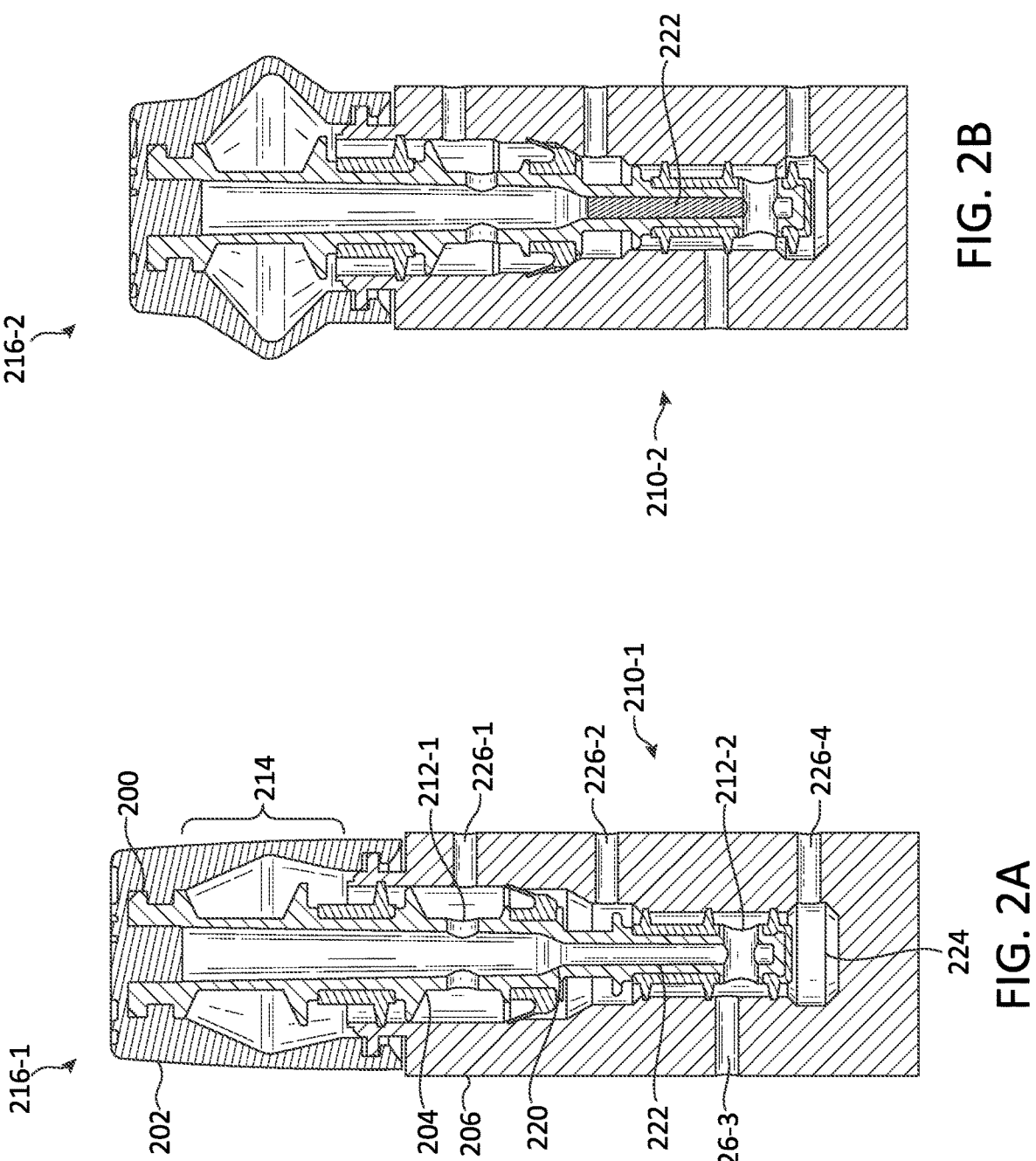
FIGS. 2A and 2B illustrate various aspects of an exemplary valve assembly in conjunction with a valve well according to one or more embodiments disclosed hereby.

FIGS. 2A and 2B illustrate various aspects of a valve assembly 200 in conjunction with a valve well 206 according to one or more embodiments of the present disclosure. More specifically, FIG. 2A includes a cross-sectional view of valve assembly 200 in a first configuration 216-1 and FIG. 2B includes a cross-sectional view of valve assembly 200 in a second configuration 216-2. The valve assembly 200 may include an interface member 200 and a valve stem 204. The interface member 200 may include an elastic section 214. The valve stem 204 may include a first orifice 212-1 and a second orifice 212-2 connected by a lumen 220. The valve well 206 may include a cavity 224 with ports 226-1, 226-2, 226-3, 226-4. In some embodiments, FIGS. 2A and/or 2B may include one or more components that are the same or similar to one or more other components of the present disclosure. For example, valve stem 204 may be the same or similar to valve stem 104. Further, one or more components of FIGS. 2A and/or 2B, or aspects thereof, may be incorporated into other embodiments of the present disclosure without departing from the scope of this disclosure. For example, the transition deposit 222 may be incorporated into valve assembly 100 without departing from the scope of this disclosure. Embodiments are not limited in this context.

In the first configuration 216-1, the valve assembly 200 may be coupled to the valve well 206 with no user input. In the second configuration 216-2, the valve assembly 200 may be coupled to the valve well 206 with user input that compresses an elastic section 214 of interface member 202 and causes the valve stem 204 to move distally within the valve well 206. In many embodiments, the second configuration may cause water input via port 226-3 to feed water, via port 226-1, into the air channel in a handle and shaft of an endoscope (not shown), and through the air nozzle at the distal end of the endoscope.

Additionally, FIGS. 2A and 2B illustrate the valve assembly 200 in different states. FIG. 2A illustrates the valve assembly 200 in a first state 210-1 and FIG. 2B illustrates the valve assembly 200 in a second state 210-2. In the first state 210-1, transition deposit 222 may be disposed in the lumen 220 in an unexposed state and in the second state 210-2 may transition to an exposed state to block the flow of water through the lumen 220. For example, transition deposit 222 may expand due to exposure to a fluid. Accordingly, the transition material may include a material that expands and hardens after exposure to a certain amount of volumetric fluid flow, such as Porex®. In other embodiments, the transition deposit may contract and/or dissolve due to exposure to a fluid (see e.g., FIGS. 5A-5C). In various embodiments, the transition deposit 222 may comprise a cylindrical insert in the lumen 220. In some embodiments, the transition deposit 222 may be a coating, such as by being powder coated onto a surface.

More generally, one or more components of valve assemblies disclosed hereby may be configured to transition from the first state to the second state in response to utilization of the valve assembly to control fluid flow through a valve well. The transition from the first state to the second state may prevent reuse in of one or more valve assemblies disclosed hereby. For example, one or more components of the valve assembly may be altered, such as by lengthening, transitioning from a first state to a second state (e.g., chemically), shortening, widening, detaching, and the like.

In several embodiments the amount of volumetric flow required for the transition deposit 222 to block the lumen 220 may be correlated to the particular use and/or amount of time a valve assembly 220 is used. For example, properly cleaning (i.e., reprocessing) an endoscope may require water flushing through the air channel of the endoscope for at least 30 seconds, requiring the valve assembly 200 to remain in the second configuration 216-2 for at least 30 seconds. Accordingly, the transition deposit 222 may be configured to require an amount of volumetric flow to transition to the second state 210-2 that is equivalent to 30 seconds of flow through the air channel. In many embodiments, this technique may simplify or improve cleaning, by requiring the valve assembly 200 just be depressed until it is fully transitioned to the second state 210-2 instead of requiring 30 seconds be timed.

In another example, a properly cleaning an endoscope may require a specific volume of water be flushed through the air channel of the endoscope. In such other examples, the transition deposit 222 may be configured to block the lumen 220 after the specific volume of water is flushed through the air channel. In this example, cleaning efficiency/reliability may be improved due to the state transition occurring directly due to volumetric flow, as opposed to an amount of time. This may be due to one or more factors, such as varying flow rates between different endoscopes or varying pressures or flow rates provided by different processor and/or insufflator setups. The processor and/or insufflator setups may comprise the source of flow fed to the valve well of the endoscope. It will be appreciated that although FIG. 2B illustrates state 210-2 while the valve assembly 200 is in the second configuration 216-2, the transition to the second state 210-2 may occur, at least partially, after the valve assembly 200 returns to the first configuration 216-1 (e.g., due to elastic section 214 comprising a biasing member to return the valve assembly 200 to the first configuration 216-1 in the absence of external input).

Utilization of a valve assembly (e.g., valve assembly 200) to control fluid flow through a valve well may include one or more of coupling the interface member to the valve well, transitioning the interface member from a first configuration to a second configuration, insertion of the distal end of the valve assembly into the proximal end of the valve well, controlling the flow of fluid through the valve well with the valve assembly 100, and removing the valve assembly from the valve well. In many embodiments, the utilization of the valve assembly to control fluid flow through a valve well may cause the transition from the first state to the second state. For example, exposing transition deposit 222 to water while using the valve assembly 200 to control fluid flow through the valve well 206 (e.g., to flush an air channel) may cause transition deposit 222 to transition from the first state 210-1 to the second state 210-2.

In various embodiments, the elastic section 214 may function as a biasing member. For example, elastic section 214 may bias the interface member 202 (and the corresponding valve assembly) into the first configuration 216-1. In other embodiments, the elastic section 214 may not include a biasing member. In such other embodiments, a spring may be used as the biasing member. In some embodiments, the walls of the elastic section 214 may have a varying in thickness and or other structures to bias interface member 202 into the first configuration 216-1. In some embodiments, the first configuration 216-1 may comprise a standby configuration and the second configuration 216-2 may comprise an actuated configuration.

In several embodiments, the interface member 202 may couple with the valve well. In several such embodiments, the interface member 202 may exert a force against the valve well 206 to bias the interface member in the first configuration 216-1. In many embodiments, the second configuration 216-2 may cause fluid to flow through the valve well 206. On the other hand, the interface member 202 (and remainder of valve assembly) may be coupled to the valve well 206 in the first configuration 216-1 without causing fluid to flow through the valve well 206. In many embodiments, the interface member 202 may be displaced distally to transition from the first configuration 216-1 to the second configuration 216-2. Further, the distal displacement of the interface member 202 moves the valve stem 204 distally within the valve well 206. In some embodiments, interface members may include one or more parts. For example, a finger of an operator may interact with a first part of the interface member and a second part of the interface member may couple with the valve well.

Figures 3A, 3B:
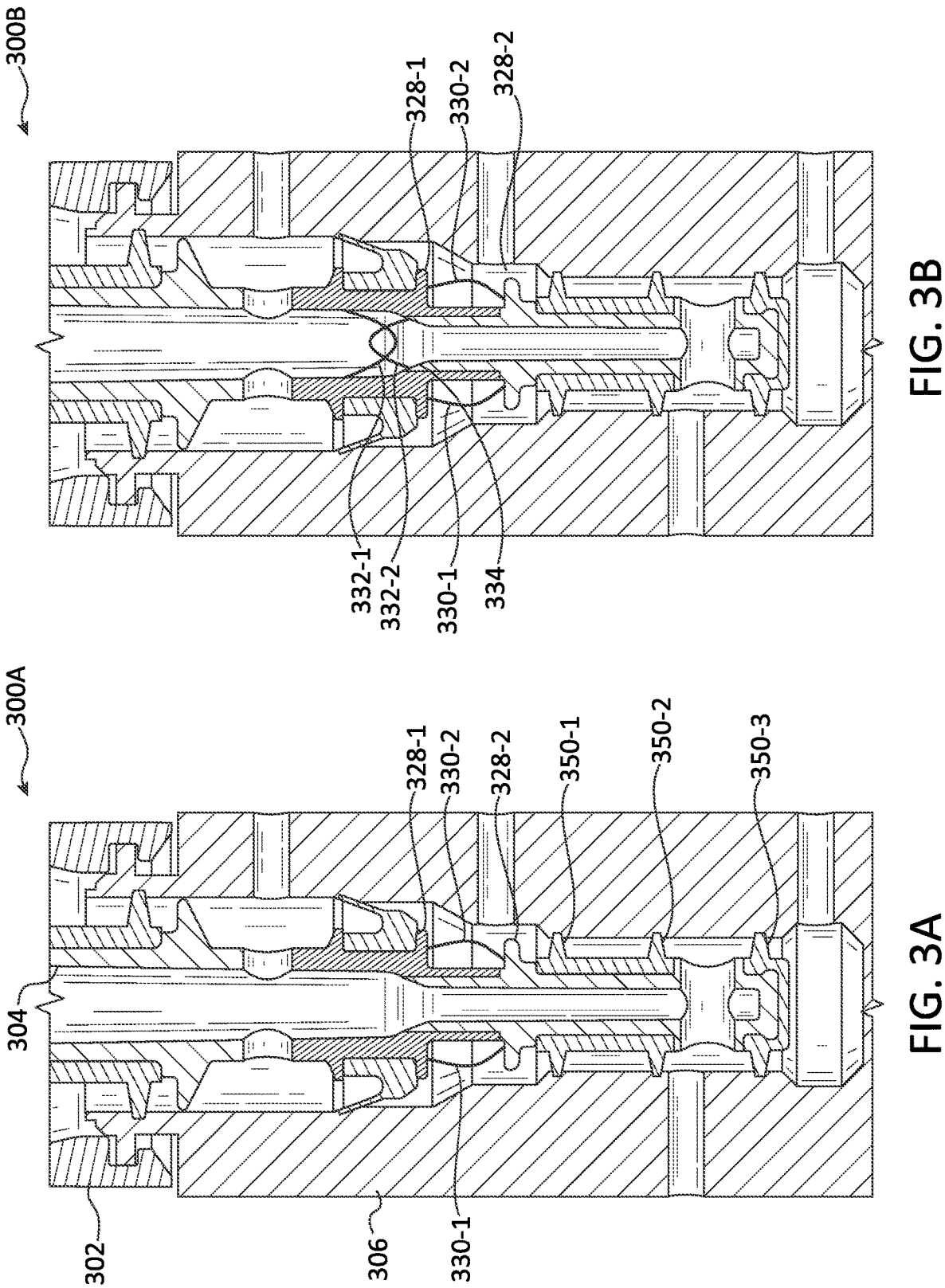
FIG. 3A illustrates various aspects of an exemplary valve assembly in conjunction with a valve well according to one or more embodiments disclosed hereby.
FIG. 3B illustrates various aspects of an exemplary valve assembly in conjunction with a valve well according to one or more embodiments disclosed hereby.

FIGS. 3A and 3B illustrate various aspects of a valve assemblies 300A, 300B in conjunction with a valve well 306 according to one or more embodiments of the present disclosure. FIG. 3A includes valve assembly 300A and valve well 306. Valve assembly 300A may include interface member 302 and valve stem 304. Valve stem 304 may include first stem portion 328-1 and second stem portion 328-2 connected by retention linkages 330-1, 330-2. The Valve assembly 300B may be the same or similar to valve assembly 300A. In FIG. 3B, valve assembly 300B may include contact surface 334 and separation linkages 332-1, 332-2 in addition to the components of valve assembly 300A. Although not labeled, in some embodiments, valve assembly 300A may include contact surface 334. In various embodiments, the first and second stem portions 328-1, 328-2 may be able to move relative to each other, such as by telescoping, to transition from a first state to a second state. In some embodiments, FIGS. 3A and/or 3B may include one or more components that are the same or similar to one or more other components of the present disclosure. For example, valve stem 304 may be the same or similar to valve stem 204. Further, one or more components of FIGS. 3A and/or 3B, or aspects thereof, may be incorporated into other embodiments of the present disclosure without departing from the scope of this disclosure. For example, the retention linkages 330-1, 330-2 may be incorporated into valve assembly 100 without departing from the scope of this disclosure. Embodiments are not limited in this context.

In many embodiments, the first and second stem portions 328-1, 328-2 may be able to move relative to each other, such as by telescoping, to transition from a first state to a second state. For instance, one or more weak points (e.g., a thin wall section, perforations, a transition deposit, poor filling, or weakened post molding) may be included, such as via molding, additive manufacturing, subtracting manufacturing, and/or powder coating, at the junction between the first and second stem portion 328. In some such instances, the weak points may allow the stem portions 328 to move relative to one another, such as during removal from the valve well or returning from an actuated configuration (e.g., the second configuration) to a standby configuration (e.g., the first configuration). In several embodiments, the retention linkages 330-1, 330-2 may keep the first and second stem portions 328 connected in the second state. In several such embodiments, the retention linkages 330 may prevent stem portion 328-2 from remaining in the valve well 306 when the valve assembly is removed. Frictional forces corresponding to radial seals 350-1, 350-2, 350-3 on the valve stem 304 contacting the cavity of the valve well may cause the first and second stem portions 328 to separate during removal from the valve well.

In one or more embodiments disclosed hereby, the first and second stem portions 328 may have loops (e.g., separation linkages) that interlock to fit each other. When pressed together (e.g., in the actuated configuration), the loops may press into solid surfaces of the opposing component (e.g., contact surface 334, contact surface 434). When the proximal portion is pulled away from the distal portion during removal, a perforated break point included on one or more of the loops may allow them to come apart. In order to retain the distal stem portion during removal and prevent it from being left in the valve well, the proximal and distal stem portions may be connected by retention linkages.

The separation linkages 332-1, 332-2 of FIG. 3B may comprise loops that break and/or become disconnected in the second state. For example, one or more of the separation linkages 332 may break apart when the valve assembly 300B is removed from the valve well 306. In various embodiments, the separation linkage 332-1 of stem portion 328-1 may push against the contact surface 334 of stem portion 328-2 when the interface member is depressed to transition the valve assembly 300B from the standby configuration to the actuated configuration. In the illustrated embodiment, the separation linkages 332 may be disposed inside of the lumen of the valve stem and the retention linkages 330 may be disposed on the exterior of the valve stem. However, valve assemblies may include one or more retention linkages and/or one or more separation linkages connecting stem portions 328 via a variety of locations without departing from the scope of this disclosure. In various embodiments, the linkages may include or be referred to as leashes. In some embodiments, the linkages may comprise a polymer and/or a metal (e.g., nitinol). In several embodiments, the linkages may be integrally molded with the valve stem.

In many embodiments, one or more components and/or features disclosed hereby may be used to differentiate cleaning valves from procedural valves. For example, retention linkages 330-1, 330-2 may differentiate valve assembly 300 from procedural valve assemblies. In another example, the interface member 302 may include one or more features for distinction, such as raised surfaces, colors, warning labels, and the like.

Figures 4A, 4B, 4C:
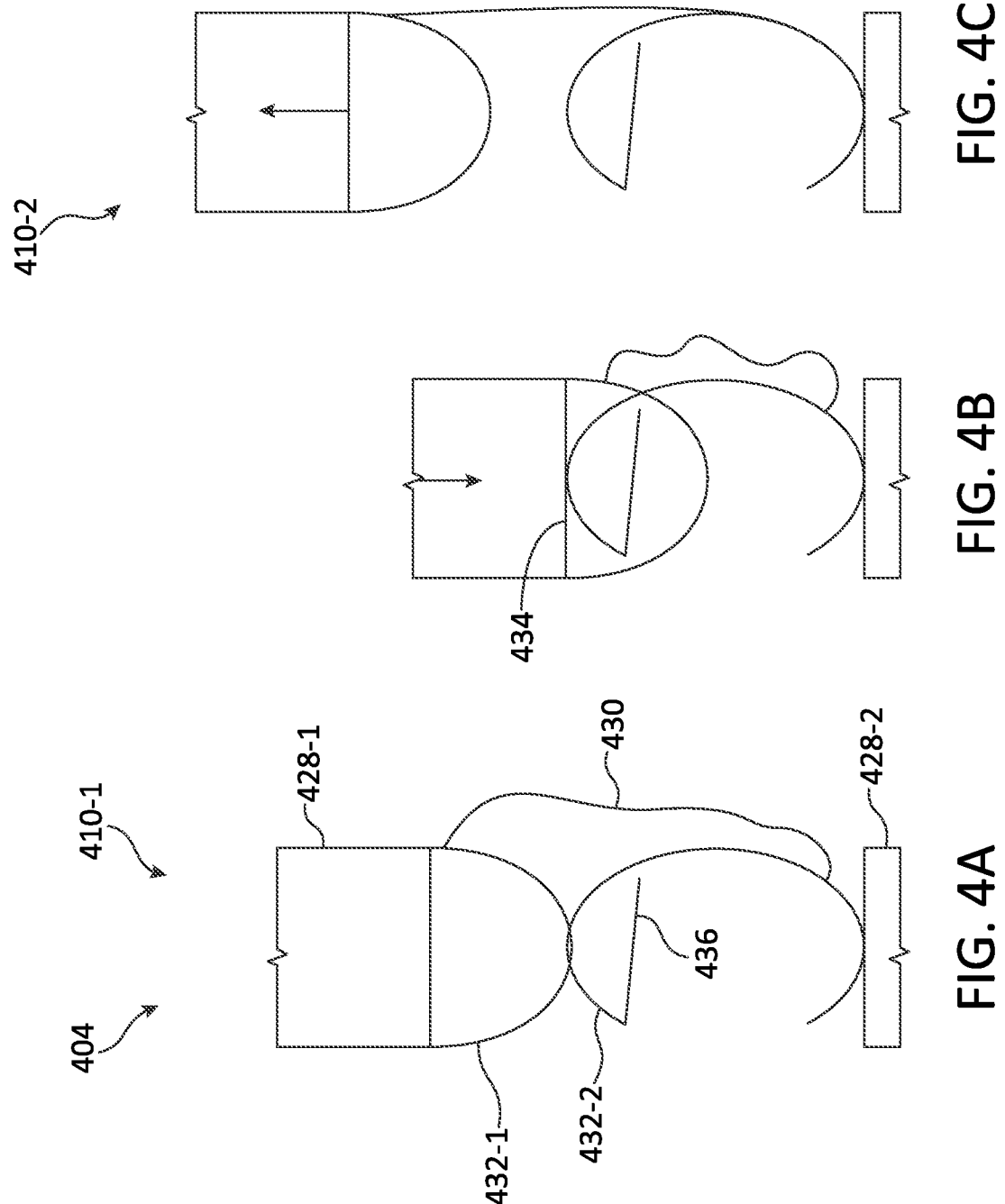
FIGS. 4A-4C illustrate various aspects of exemplary valve stem portions according to one or more embodiments disclosed hereby.

FIGS. 4A-4C illustrate various aspects of valve stem portions 428-1, 428-2 of valve stem 404 according to one or more embodiments of the present disclosure. FIGS. 4A-4C illustrate an alternative embodiment of a valve stem with first and second stem portions 428-1, 428-2, retention linkage 430, and separations linkages 432-1, 432-2. In the illustrated embodiment, separation linkage 432-2 is attached to the proximal end of stem portion 428-2 and includes arm 436. In some embodiments, arm 436 may pivot and/or be biased into a certain position by a biasing member (e.g., spring). Separation linkage 432-1 is attached to the distal end of stem portion 428-1, which includes contact surface 434. In some embodiments, FIGS. 4A-4C may include one or more components that are the same or similar to one or more other components of the present disclosure. For example, stem portions 428-1, 428-2 may be the same or similar to stem portions 328-1, 328-2. Further, one or more components of FIGS. 4A-4C, or aspects thereof, may be incorporated into other embodiments of the present disclosure without departing from the scope of this disclosure. For example, the separation linkages 432-1, 432-2 may be incorporated into valve stem 304 without departing from the scope of this disclosure. Embodiments are not limited in this context.

In various embodiments, FIGS. 4A-4C illustrates the first stem portion 428-1 with a strong, non-perforated loop and the second stem portion 428-2 with a spring-loaded gate (i.e., arm 436) loop (e.g., separation linkage 432-2), like a carabiner except the arm 436 may be biased open instead of in the closed position. More specifically, FIG. 4A illustrates the valve stem 404 in the first state 410-1, which may correspond to the standby configuration; FIG. 4B illustrates the valve stem 404 in a transition state, which may correspond to the actuated configuration; and FIG. 4C illustrates the valve stem 404 in the second state 410-2, which may occur when the valve stem 404 is removed from a valve well after the transition state. In the transition state, contact surface 434 may push against a proximal end of separation linkage 432-2 to push the second stem portion 428-2 distally in a valve well. Further, the distal end of separation linkage—432-1 may push past (e.g., by pushing open) the arm 436 and allow the arm 436 to reclose. When the valve stem is removed the reclosed arm 436 forces the separation linkages 432 to separate.

FIGS. 5A-5C illustrate various aspects of valve stem portions 528-1, 528-2 according to one or more embodiments of the present disclosure. The valve stem 504 may include stem portions 528-1, 528-2 and retention linkages 530-1, 530-2. FIG. 5A illustrates valve stem 504 in a first state 510-1 and including transition deposit 522. FIGS. 5B and 5C illustrate valve stem 504 in a second state 510-2. In some embodiments, FIGS. 5A-5C may include one or more components that are the same or similar to one or more other components of the present disclosure. For example, stem portions 528-1, 528-2 may be the same or similar to stem portions 328-1, 328-2. Further, one or more components of FIGS. 5A-5C, or aspects thereof, may be incorporated into other embodiments of the present disclosure without departing from the scope of this disclosure. For example, the stem portions 328-1, 328-2 may be incorporated into valve stem 104 without departing from the scope of this disclosure. Embodiments are not limited in this context.

In the first state 510-1, transition deposit 522 may lock the stem portions 528-1, 528-2 in a compressed position relative to each other. However, in the second state 510-2, transition deposit 522 may be absent and the stem portions 528 may be in an extended position relative to each other. Accordingly, in the absence of transition deposit 522, stem portions 528 may move relative to one another, such as by telescoping. In many embodiments, transition deposit 522 may operate in an opposite manner as the transition deposit 222, such as by dissolving when exposed to a fluid.

In many embodiments, the extended position may expose one or more radial openings 533 to prevent reuse of the valve stem 504. In some embodiments, the valve stem 504 may include one or more features to lock the stem portions 528 in the extended state. For example, a transition deposit similar to transition deposit 222 may be used to lock the stem portions 528 in the extended state. In other embodiments, the stem portions 528 may freely move relative to one another in the second state 510-2. In various embodiments, controlling fluid flow through a valve well may cause transition deposit 522 to dissolve (or at least weaken), allowing the valve stem to transition into state 510-2 when it is removed from a valve well. In several embodiments, transition deposit 522 may comprise a glue, such as polyvinyl acetate.

Retention linkages 530-1, 530-2 may include corresponding features that prevent stem portions 528 from separating when they are removed from a valve well. For example, retention linkages 530 may include a collar and/or ledge. In another example, retention linkage 530-1 may include a channel and retention linkage 530-2 may include a protrusion that moves within the channel.

Figure 6A:
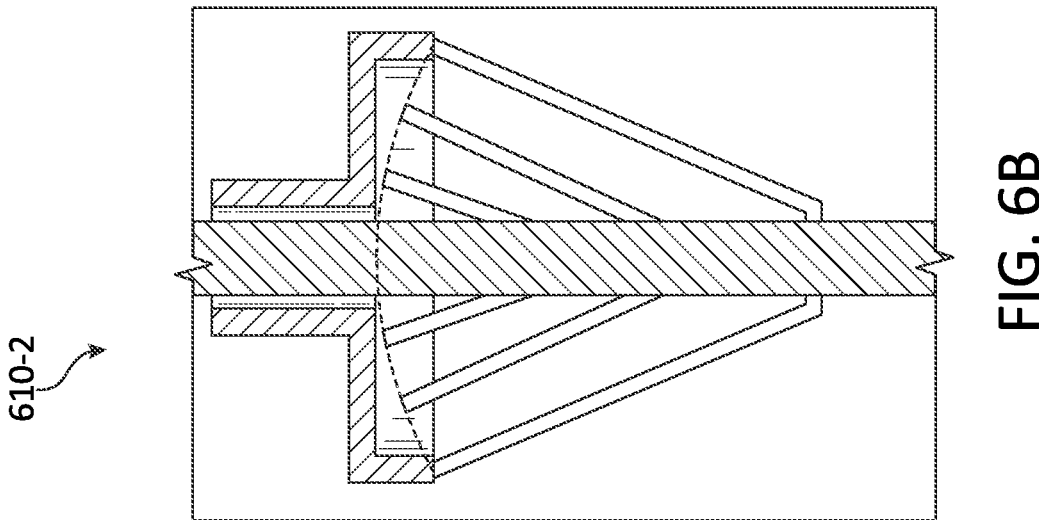
FIGS. 6A and 6B illustrate an exemplary valve stem with radial legs according to one or more embodiments disclosed hereby.
Figure 6B:
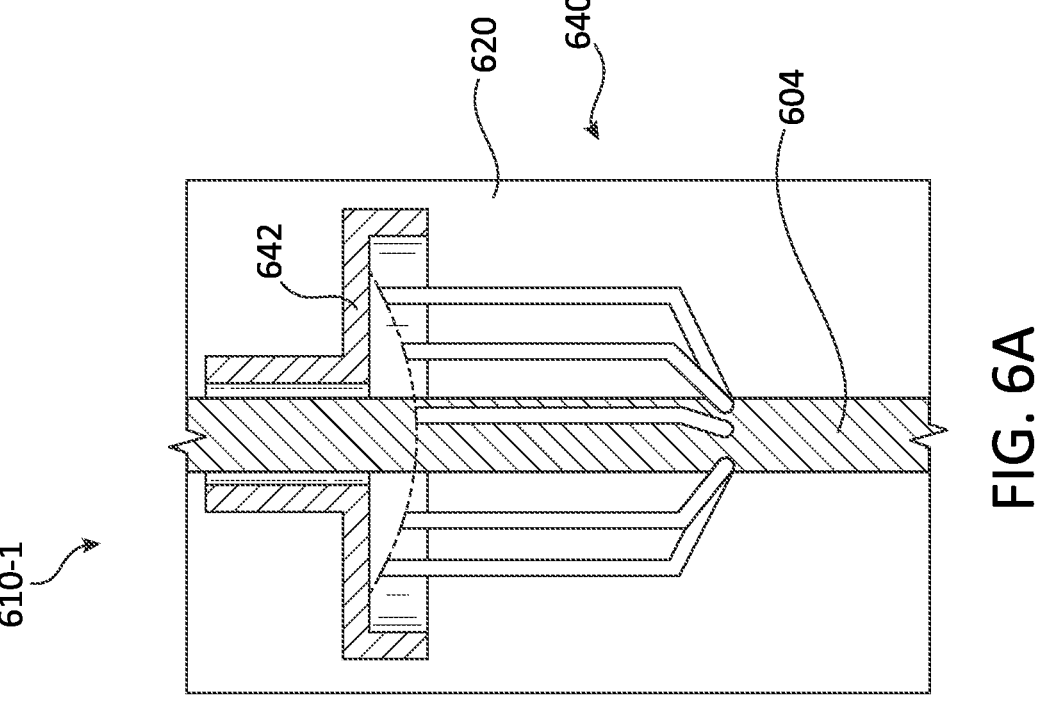

FIGS. 6A and 6B illustrate a valve stem 604 with radial legs 640 according to one or more embodiments of the present disclosure. The valve stem 604 may additionally include hat 642. FIG. 6A may illustrate the valve stem 604 in a first state 610-1 with the hat 642 retaining the one or more radial legs 640 proximate the valve stem 604. FIG. 6B may illustrate the valve stem 604 in a second state 610-2 with the radial legs 640 released by the hat 642. In some embodiments, FIGS. 6A and/or 6B may include one or more components that are the same or similar to one or more other components of the present disclosure. For example, valve stem 604 may be the same or similar to valve stem 104. Further, one or more components of FIGS. 6A and/or 6B, or aspects thereof, may be incorporated into other embodiments of the present disclosure without departing from the scope of this disclosure. For example, the radial legs 640 may be incorporated into valve assembly 200 without departing from the scope of this disclosure. Embodiments are not limited in this context.

In various embodiments, valve stem 604 may include one or more radial legs 640 with a first end connected to the valve stem 604. The hat 642 may retain the second end of the radial legs 640 proximate the shaft of the valve stem 604 until the valve stem is depressed. In various embodiments, the hat 642 may include one or more of a cylindrical cuff, a containing tray/box/guard, and the like. In many embodiments, the radial legs 640 are in a shortened configuration when they are retained by hat 642. For example, the radial legs may include a bend or a bow in state 610-1. In some such examples, the bend or the bow may cause the radial legs 640 to expand radially and extend proximally when released by the hat. In some embodiments, biasing members, such as springs, may be used to cause the radial legs 640 to expand radially and extend proximally.

In the second state 610-2, the legs may extend and lock, such as against the hat 642, to cause the valve stem 604 to lengthen and become inoperable to control the flow of fluid through a valve well. For example, the radial legs 640 may be fixed to the valve stem 604 and hat 642 may be slidably coupled to the valve stem 604. Accordingly, as the valve stem 604 is depressed distally (e.g., to transition into the actuated configuration) the second ends of the radial legs 640 may move distally enough to no longer be retained by the hat 640. When the radial legs 640 are not retained by the hat 642, the radial legs 640 may lengthen. When the valve stem 604 returns proximally (e.g., to transition back the standby configuration) the radial legs 640 may lock, in the lengthened position, against the hat 642 to increase the overall length of the valve stem 604.

This application relates to, and incorporates by reference in their entireties for all purposes, U.S. patent application Ser. No. 16/868,325, titled "Devices, Systems, Methods, and Designs for Medical Cleaning Valves, filed May 6, 2020.

This application relates to, and incorporates by reference in their entireties for all purposes, U.S. patent application Ser. No. 16/868,329, titled "Devices, Systems, and Methods for Medical Cleaning Valves," filed May 6, 2020.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method disclosed hereby without departing from the concept, spirit, and scope of the disclosure.

What is claimed is:

1. A single-use valve assembly comprising:
an interface member;
a valve stem to which the interface member is removably couplable, the valve stem including a proximal portion, a distal portion, two or more orifices, and a lumen in fluid communication with first and second orifices of the two or more orifices; and
a transition deposit in the lumen,
wherein the valve assembly is configured to transition from a first state in which the valve assembly is utilized to control fluid flow through a valve well by adjusting between a first configuration and a second configuration to a second state in which reuse of the valve assembly is prevented in response to utilization of the valve assembly in the first state to control fluid flow through the valve well, wherein in the second state, the transition deposit is transitioned from a first deposit state to a second deposit state to block the lumen and prevent reuse of the valve assembly to control the fluid flow through the valve well in response to adjusting the valve assembly between first configuration and the second configuration.

2. The valve assembly of claim 1, wherein the fluid communication between the first and second orifices via the lumen is blocked in the second state.

3. The valve assembly of claim 2, wherein the transition deposit comprises a material configured to expand and fill a portion of the lumen when the material is exposed to a liquid in response to adjusting the valve assembly between the first configuration and the second configuration.

4. The valve assembly of claim 1, wherein the proximal portion and the distal portion of the valve stem decouple to transition from the first state to the second state.

5. The valve assembly of claim 1, wherein the proximal and distal portions of the valve stem are connected by a retention linkage and a separation linkage in the first state and the proximal and distal portions of the valve stem are connected by the retention linkage and not the separation linkage in the second state.

6. The valve assembly of claim 5, wherein the separation linkage or the retention linkage is disposed within the lumen.

7. The valve assembly of claim 5, wherein the separation linkage or the retention linkage is disposed outside of the lumen.

8. The valve assembly of claim 1, wherein utilization of the valve assembly to control the fluid flow through the valve well comprises one or both of insertion of the valve stem into the valve well and removal of the valve stem from the valve well.

9. The valve assembly of claim 1, wherein the proximal portion of the valve stem is fixed relative to the distal portion of the valve stem by a molded weak point in the first state, and the proximal portion of the valve stem is slidably coupled to the distal portion of the valve stem in the second state.

10. The valve assembly of claim 9, wherein utilization of the valve assembly to control fluid flow through the valve well breaks the molded weak point to transition the valve assembly from the first state to the second state.

11. The valve assembly of claim 1, wherein the proximal portion of the valve stem is fixed relative to the distal portion of the valve stem by a transition deposit in the first state, and the proximal portion of the valve stem is slidably coupled to the distal portion of the valve stem in the second state.

12. The valve assembly of claim 11, wherein exposure of the transition deposit to a liquid from utilization of the valve assembly to control fluid flow through the valve well dissolves the transition deposit to transition the valve assembly from the first state to the second state.

13. The valve assembly of claim 1, comprising a plurality of radial legs with first and second ends, wherein the first ends are pivotally connected to the valve stem.

14. The valve assembly of claim 13, wherein the second ends are retained proximate to the valve stem by a hat slidably coupled to the valve stem in the first state and the second ends are released by the hat in the second state.

15. A system, comprising:
a valve well comprising a cavity with two or more ports; and
a single-use valve comprising:
a valve stem including a proximal portion, a distal portion, two or more orifices, and a lumen in fluid communication with a first orifice and a second orifice of the two or more orifices, and
an interface member coupled to the valve well and the valve stem, wherein the interface member is configured to change from a depressed state to an extended state;
wherein the single use valve is configured to transition from a first state to a second state in response to utilization of the single use valve in the first state between a first configuration and a second configuration to control fluid flow through the valve well, wherein the second state of the single use valve prevents the fluid flow through the valve well between the first orifice and the second orifice and prevents reuse of the single-use valve in the first state.

16. The system of claim 15, wherein utilization of the single use valve to control the fluid flow through the valve well comprises one or more of insertion of the valve stem into the valve well, controlling the fluid flow through the valve well, and removal of the valve stem from the valve well.

17. The system of claim 15, wherein the fluid communication between the first and second orifices via the lumen is blocked in the second state.

18. The system of claim 15, wherein the proximal portion and the distal portion of the valve stem decouple to transition from the first state to the second state.

19. A valve assembly comprising:
an interface member, wherein the interface member is configured to change from an extended state to a depressed state when used to control fluid flow through a valve well; and
a valve stem to which the interface member is removably couplable, the valve stem including a proximal portion, a distal portion, two or more orifices, and a lumen in fluid communication with first and second orifices of the two or more orifices, wherein the valve assembly is configured to transition from a first state to a second state in response to use of the valve assembly in the first state between a first configuration and a second configuration to control the fluid flow through the lumen and the valve well, and wherein in the second state of the valve assembly, the lumen is blocked to prevent reuse of the valve assembly to control the fluid flow through the lumen and the valve well by adjusting the valve assembly between the first configuration and the second configuration.

* * * * *